United States Patent
Bertelo

(10) Patent No.: US 10,259,761 B2
(45) Date of Patent: Apr. 16, 2019

(54) METHOD FOR PRODUCING FLUORINATED OLEFINS

(71) Applicant: Arkema Inc., King of Prussia, PA (US)

(72) Inventor: Christopher A. Bertelo, Doylestown, PA (US)

(73) Assignee: ARKEMA INC., King of Prussia, PA (US)

( * ) Notice: Subject to any disclaimer, the term of this patent is extended or adjusted under 35 U.S.C. 154(b) by 0 days.

(21) Appl. No.: 15/571,079

(22) PCT Filed: Jun. 1, 2016

(86) PCT No.: PCT/US2016/035140
§ 371 (c)(1),
(2) Date: Nov. 1, 2017

(87) PCT Pub. No.: WO2016/196538
PCT Pub. Date: Dec. 8, 2016

(65) Prior Publication Data
US 2018/0162795 A1    Jun. 14, 2018

Related U.S. Application Data

(60) Provisional application No. 62/170,716, filed on Jun. 4, 2015.

(51) Int. Cl.
C07C 17/278    (2006.01)
C07C 17/269    (2006.01)
C07C 21/18     (2006.01)

(52) U.S. Cl.
CPC .......... *C07C 17/278* (2013.01); *C07C 17/269* (2013.01)

(58) Field of Classification Search
CPC ......... C07C 17/23; C07C 17/25; C07C 21/18; C07C 17/269
See application file for complete search history.

(56) References Cited

U.S. PATENT DOCUMENTS

| | | |
|---|---|---|
| 3,101,304 A | 8/1963 | Wist |
| 5,026,460 A | 6/1991 | Dapperheld |
| 5,382,720 A | 1/1995 | Ikawa et al. |
| 7,135,601 B2 | 11/2006 | Mukhopadhyay |

OTHER PUBLICATIONS

Aviyente, V., et al. Analysis of the Kinetics of the Thermal Decomposition of Pentafluoroethane, Canadian-Journal of Chemistry, vol. 68, 1990, pp. 1332-1337; abstract.

*Primary Examiner* — Jafar F Parsa
(74) *Attorney, Agent, or Firm* — Steven D. Boyd

(57) ABSTRACT

Fluorinated olefins are produced in a reductive coupling reaction by contacting a first reactant with a second reactant in the gas phase under an inert atmosphere at a temperature of at least 500 C. The first reactant may be, for example, a hydrofluorocarbon containing one or two carbon atoms, while the second reactant may be, for example, a two to four carbon hydrohalocarbon (e.g., a hydrofluorocarbon) or hydrocarbon.

20 Claims, No Drawings

METHOD FOR PRODUCING FLUORINATED OLEFINS

This present application is the national phase under 35 USC § 371 of prior PCT International Application Number PCT/US2016/035140 filed Jun. 1, 2016 which designated the United States of America and claimed priority to U.S. Provisional Patent Application Ser. No. 62/170,716 filed Jun. 4, 2015.

FIELD OF THE INVENTION

The present invention pertains to methods for producing fluorinated olefins, wherein a mixture of reactants (including at least one hydrofluorocarbon) is subjected to conditions effective to achieve reductive coupling of the starting materials.

DISCUSSION OF THE RELATED ART

The Montreal Protocol for the protection of the ozone layer mandated the phase-out of the use of chlorofluorocarbons (CFCs). Materials friendlier to the ozone layer, such as hydrofluorocarbons (HFCs), e.g., HFC-134a, replaced chlorofluorocarbons. The latter compounds have proven to be greenhouse gases, causing global warming. They were regulated by the Kyoto Protocol on Climate Change. With the continued concern over global climate change there is an increasing need to develop technologies to replace those with high ozone depletion potential (ODP) and high global warming potential (GWP). Although hydrofluorocarbons (HFCs), being non-ozone depleting compounds, have been identified as alternatives to chlorofluorocarbons (CFCs) and hydrochlorofluorocarbons (HCFCs) as refrigerants, extinguishers, blowing agents, foaming agents, dielectrics, support fluids, agents for abrasives, intermediates for the production of other types of fluorinated substances, drying agents, solvents, cleaning agents and heat transfer fluids, they still tend to have significant GWP. Hydrofluoroolefins (HFO) have been identified as potential alternatives with zero ODP and low GWP.

A number of different procedures for making fluoroolefins have been disclosed. However, there is still a need to provide improved processes for producing fluoroolefins using alternative feedstocks and/or reaction conditions.

SUMMARY OF THE INVENTION

One embodiment of the present invention provides a method of making a fluorinated olefin comprising contacting a first reactant with a second reactant in the gas phase under an inert atmosphere at a temperature of at least 500° C. (in certain embodiments, 500° C. to 1200° C.; in other embodiments, 600° C. to 1100° C.), wherein:

the first reactant has structure (Ia):

      (Ia)

where X is F, Cl, Br or I and y is 1 or 2;
or structure (Ib):

      (Ib)

where X' is F, Cl, Br or I, y' is 1, 2 or 3, and z is 1 or 2; and
the second reactant has structure (II):

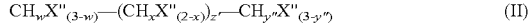      (II)

where each X" is independently selected from F, Cl, Br or I, w is 0, 1, 2 or 3, x is 0, 1 or 2, y" is 0, 1, 2 or 3, subject to the proviso that w, x and y" are not all 0, and z' is 0, 1 or 2 (in certain embodiments, z' is 0 or 1).

In certain embodiments, the second reactant contains at least one X". For example, the second reactant may contain one, two, three, four, five or more X" groups. In other embodiments, the second reactant contains at least one X" which is F.

In one embodiment, the first reactant has structure (Ia) and X is Cl. In another embodiment, the first reactant has structure (Ib) and X' is Cl. In a further embodiment, z' in the second reactant is 0 or 1. In a still further embodiment, the first reactant has structure (Ia), X is Cl and z' in the second reactant having structure (II) is 0 or 1.

In a further embodiment, only one X" in the second reactant is a halide other than F. In still another embodiment, each X" in the second reactant is F.

In certain embodiments, the second reactant contains at least two X" groups and each X" in the second reactant is F, subject to the proviso that one X" in the second reactant is Cl. In other embodiments, the second reactant contains at least three X" groups and each X" in the second reactant is F, subject to the proviso that two X" groups are Cl.

The contacting between the first reactant and the second reactant may be carried out in the absence of catalyst or in the presence of catalyst. If catalyst is present, the catalyst may be comprised of at least one metal, such as at least one transition metal.

In one aspect of the invention, the first reactant may be selected from the group consisting of $CHF_2Cl$, $CH_2FCl$, $CH_2ClCF_3$, $C_2H_4ClF$ (e.g., $CH_2ClCH_2F$), $C_2H_3ClF_2$ (e.g., $CH_2ClCHF_2$), $C_2H_2F_4$ (e.g., $CH_2FCF_3$) and $C_2HCl_2F_3$ (e.g., $CHCl_2CF_3$). In another aspect, the second reactant may be a C2 (two carbon) compound selected from the group consisting of $C_2H_3F_3$ (e.g., $CH_2F$—$CHF_2$, $CH_3$—$CF_3$), $C_2H_4F_2$ (e.g., $CH_3$—$CHF_2$), $C_2H_5F$ ($CH_3$—$CH_2F$), $C_2H_2F_4$ (e.g., $CH_2F$—$CF_3$) and $C_2HF_5$ ($CHF_2$—$CF_3$), as well as analogous compounds in which at least one (but not all) of the hydrogens is replaced by Cl and/or Br (such as CHClF—$CHF_2$, for example, which is an analogue of $CH_2F$—$CHF_2$) and analogous compounds in which at least one (but not all) of the fluorines is replaced by Cl and/or Br (such as $CH_2Cl$—$CHF_2$, which is an analogue of $CH_2F$—$CHF_2$).

Exemplary fluorinated olefins which may be produced in accordance with the present invention include, but are not limited to, $F_2C$=CF—$CF_3$, cis and trans FHC=CF—$CF_3$, $H_2C$=CF—$CF_3$, $H_2C$=CCl—$CF_3$, cis and trans ClHC=CH—$CF_3$ and cis and trans FHC=CH—$CF_3$. In some cases, mixtures of different fluorinated olefins are produced.

DETAILED DESCRIPTION OF THE INVENTION

The methods of the present invention comprise converting a compound of formula (Ia) and/or (Ib) ("the first reactant") to a fluoroolefin (fluorinated olefin), for example a C3, C4 and/or C5 fluoroolefin, wherein the first reactant is reacted with at least one compound of formula (II) ("the second reactant"). This reaction results in carbon-carbon bond formation between the first reactant and the second reactant and loss of hydrogen ($H_2$) and thus may be considered to be a reductive coupling reaction.

An illustrative example of such a reaction is as follows:

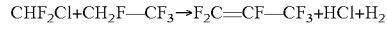

In certain advantageous embodiments of the invention, both the first reactant and the second reactant are hydrofluorocarbons, i.e., organic compounds containing at least one hydrogen atom and at least one fluorine atom per molecule. In other embodiments, however, the first reactant is a hydrofluorocarbon and the second reactant is a hydrocarbon (i.e., an organic compound containing only carbon and hydrogen). The first and second reactants are saturated compounds. In certain embodiments, one or both of the first reactant and the second reactant consists only of carbon, hydrogen and fluorine atoms. In other embodiments, the first and/or second reactant may contain one or more elements other than C, H and F, such as one or more halide atoms other than F (in particular, Cl).

The first reactant may have structure (Ia):

  (Ia)

where X is F, Cl, Br or I and y is 1 or 2;
or structure (Ib):

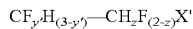  (Ib)

where X' is F, Cl, Br or I, y' is 1, 2 or 3, and z is 1 or 2.

In one embodiment, the first reactant has structure (Ia) and X is Cl. In another embodiment, the first reactant has structure (Ib) and X' is Cl.

Examples of compounds suitable for use as the first reactant in the process of the present invention include, but are not limited to, $CHF_2Cl$, $CH_2FCl$, $CH_2ClCF_3$, $CH_2ClCH_2F$, $CH_2ClCHF_2$, $CH_2FCF_3$ and $CHCl_2CF_3$.

The second reactant has structure (II):

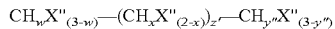  (II)

where each X" is independently selected from F, Cl, Br or I, w is 0, 1, 2 or 3, x is 0, 1 or 2, y" is 0, 1, 2 or 3, subject to the proviso that w, x and y" are not all 0, and z' is 0, 1 or 2. Thus, the second reactant may be a hydrocarbon (when w=3, x=2 and y"=3). However, in other embodiments the second reactant is a hydrohalocarbon (containing at least one X"), which may be a hydrofluorocarbon (containing at least one F).

In one embodiment, z' in the second reactant is 0 or 1. In a further embodiment, only one X" in the second reactant is a halide other than F. In still another embodiment, each X" in the second reactant is F.

In certain embodiments, the second reactant contains at least two X" groups and each X" in the second reactant is F, subject to the proviso that one X" in the second reactant is Cl. In other embodiments, the second reactant contains at least three X" groups and each X" in the second reactant is F, subject to the proviso that two X" groups are Cl.

Non-limiting examples of compounds suitable for use as the second reactant in the process of the present invention include, but are not limited to, compounds selected from the group consisting of $CH_2F-CHF_2$, $CH_3-CHF_2$, $CH_3-CF_3$, $CH_3-CH_2F$, $CH_2F-CF_3$, $CHF_2-CF_3$ and chlorinated analogues thereof containing at least one Cl, at least one F and at least one H per molecule.

Hydrofluorocarbon and hydrocarbon compounds useful as starting materials in the present invention are known in the art and may be prepared using any suitable method.

In certain embodiments, the present reaction is carried out under conditions effective to provide a conversion of at least one of the first reactant or the second reactant of at least about 40%, at least about 55%, at least about 70%, at least about 90%, or even about 100%. In other certain embodiments, the reaction of the first and second reactants to produce at least one fluoroolefin is conducted under conditions effective to provide a selectivity to fluoroolefin (either a single fluoroolefin or fluoroolefins generally) of at least about 25%, at least about 40%, at least about 70%, or at least about 90%.

This reaction step can be carried out in the gas phase and it is contemplated that the reaction can be carried out continuously (using a plug flow continuous system, for example). In certain embodiments, the reaction is carried out in the presence of catalyst. However, the use of catalyst is optional; in other embodiments of the invention, the reaction is carried out in the absence of catalyst.

In certain embodiments, a stream containing the first reactant and a stream containing the second reactant are introduced into a reaction vessel. In other embodiments, a single stream in which the first reactant and second reactant are pre-mixed is introduced into a reaction vessel. The aforementioned streams may be preheated, so as to avoid condensation. In one embodiment, both streams are gas streams (i.e., the streams are in the gas phase). The vessel may be comprised of materials which are resistant to corrosion such as Hastelloy, Inconel, Monel and/or fluoropolymer linings. The vessel may optionally contain a catalyst, for example a fixed or fluid catalyst bed, packed with a suitable catalyst, with suitable means to heat the reaction mixture to the desired reaction temperature. Any suitable vessel type, such as a tank, tubular reactor or plug flow reactor, may be utilized. In one embodiment, the vessel does not contain a catalyst.

If a catalyst is to be present during the contacting of the first and second reactants, any of a number of different types of catalysts can be employed. Such catalysts may increase the rate of reaction and/or improve selectivity to the desired fluoroolefin. The catalyst may be supported or unsupported. In certain embodiments, the catalyst is comprised of at least one metal, in particular at least one transition metal such as nickel. Other types of catalysts that may be employed include, for example, Pt/C (platinum on carbon), CaO and BaO catalysts. It is expected that many other catalysts may be used depending on the requirements of particular embodiments in view of the teachings contained herein. Of course, two or more any of these catalysts, or other catalysts not named here, may be used in combination.

While it is contemplated that a wide variety of reaction temperatures may be used in the present invention, depending on relevant factors such as the catalyst (if any) being used and the most desired reaction product, it is generally preferred that the reaction temperature for the reductive coupling of the first and second reactants be at least 500° C. or, in other embodiments, at least 600° C., or even higher. In certain embodiments, the reaction temperature is not greater than 1200° C. or not greater than 1100° C. Gradient temperatures may be employed wherein, for example, a stream comprised of the first and second reactants is initially exposed to a first temperature and then subsequently exposed to a second temperature which is higher or lower than the first temperature.

In general, it is also contemplated that a wide variety of reaction pressures may be used, depending again on relevant factors such as whether a catalyst is used and the specific catalyst being used and the most desired reaction product. The reaction pressure can be, for example, superatmospheric, atmospheric or subatmospheric, and in certain embodiments of the invention is from about 15 to about 120 psia.

In certain embodiments, an inert diluent gas or mixture of inert diluent gasses, such as nitrogen or argon, may be used in combination with the other reactor feeds. When such a diluent is used, it is generally preferred that the first and second reactants comprise, in total, from about 5% to greater than 99% by weight based on the combined weight of diluent and reactants. The diluent gas may comprise less than 5 volume % oxygen, less than 1 volume % oxygen, or less than 0.1 volume % oxygen, in various exemplary embodiments of the invention, the balance (if any) being one or more inert gasses such as nitrogen. As used herein, the phrase "under an inert atmosphere" means that less than 5 volume % oxygen (e.g., less than 1 volume % oxygen or less than 0.1 volume % oxygen) is present in the gas phase reaction mixture as the first and second reactants are being contacted with each other under conditions effective to form fluorinated olefin.

The stoichiometry of the first reactant and the second reactant during the contacting step of the method of the present invention may be varied and controlled as may be desired to achieve a particular outcome. However, the molar ratio of first reactant to second reactant (first reactant:second reactant) may be, in various exemplary embodiments of the invention, from about 10:1 to about 1:10, about 5:1 to about 1:5, or about 2:1 to about 1:2.

Contact times, as expressed herein, are based on the time the first reactant and the second reactant spend in that portion of a vessel that is within 100° C. of the temperature indicated for the operation. In various embodiments of the present invention, the contact time between the first reactant and the second reactant is from about 0.01 seconds to about 100 seconds or from about 0.1 seconds to about 10 seconds.

In the embodiments of the invention wherein a catalyst is present as the first and second reactants are reacted with each other, it is contemplated that the amount of catalyst used will vary depending on the particular parameters present in each embodiment. In certain embodiments, the contact time (i.e., the contact time between the reactants and the catalyst) is from about 0.01 seconds to about 100 seconds or from about 0.1 second to about 10 seconds.

Following the reaction of the first and second reactants, the reaction product thereby obtained, containing fluoroolefin, may be subjected to further processing as may be desired to purify and/or isolate the fluoroolefin. For example, the reaction product may be fractionated, using techniques such as fractional condensation, fractional distillation, and/or adsorption so as to separate fluoroolefin from other components of the reaction product, such as unreacted first reactant, unreacted second reactant and/or byproducts (i.e., products other than fluoroolefin, such as $H_2$, hydrogen halide, and non-fluoroolefin organic compounds). If the reaction product contains acid (e.g., HCl or other hydrogen halide acid), it may be subjected to a neutralization or scrubbing step so as to provide fluoroolefin with a low level of acidity. The reaction product may initially be in the gas phase; recovery of the desired fluoroolefin may therefore involve condensation (conversion of the gaseous fluoroolefin to a liquid state, with separation of the fluoroolefin from other components of the reaction product being performed before and/or after condensation). Unreacted reactant(s) separated from the fluoroolefin may be recycled back into the vessel and subjected to further reaction.

The particular fluorinated olefin or mixture of fluorinated olefins obtained as a result of carrying out the method of the present invention will depend upon the starting materials and reaction conditions selected, but examples of fluorinated olefins which can be prepared include, without limitation, $F_2C=CF-CF_3$, cis and/or trans $FHC=CF-CF_3$, $H_2C=CF-CF_3$, $H_2C=CCl-CF_3$, cis and/or trans $ClHC=CH-CF_3$ and cis and/or trans $FHC=CH-CF_3$.

Aspects of the invention include:
1. A method of making a fluorinated olefin comprising contacting a first reactant with a second reactant in the gas phase under an inert atmosphere at a temperature of at least 500° C., wherein:
the first reactant has structure (Ia):

$$CH_yF_{(3-y)}X \qquad (Ia)$$

where X is F, Cl, Br or I and y is 1 or 2;
or structure (Ib):

$$CF_{y'}H_{(3-y')}—CH_zF_{(2-z)}X' \qquad (Ib)$$

where X' is F, Cl, Br or I, y' is 1, 2 or 3, and z is 1 or 2; and
the second reactant has structure (II):

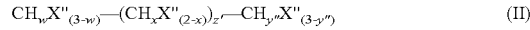
$$CH_wX''_{(3-w)}—(CH_xX''_{(2-x)})_{z'}—CH_{y''}X''_{(3-y'')} \qquad (II)$$

where each X" is independently selected from F, Cl, Br or I, w is 0, 1, 2 or 3, x is 0, 1 or 2, y" is 0, 1, 2 or 3, subject to the proviso that w, x and y" in structure (II) are not all 0, and z' is 0, 1 or 2.
2. The method of aspect 1, wherein the second reactant contains at least one X".
3. The method of aspects 1 and 2, wherein the second reactant contains at least one F.
4. The method of any of the previous aspects, wherein the first reactant has structure (Ia) and X is Cl.
5. The method of any of the previous aspects, wherein the first reactant has structure (Ib) and X' is Cl.
6. The method of any of the previous aspects, wherein z' in the second reactant is 0 or 1.
7. The method of any of the previous aspects, wherein the first reactant has structure (Ia), X is Cl and z' in the second reactant is 0 or 1.
8. The method of any of the previous aspects, wherein only one X" in the second reactant is a halide other than F.
9. The method of any of the previous aspects, wherein each X" in the second reactant is F.
10. The method of claim 1, wherein the second reactant contains at least two X" groups and each X" in the second reactant is F, subject to the proviso that one X" in the second reactant is Cl.
11. The method of any of the previous aspects, wherein the second reactant contains at least three X" groups and each X" in the second reactant is F, subject to the proviso that two X" groups are Cl.
12. The method of any of the previous aspects, wherein the temperature is from 500° C. to 1200° C.
13. The method of any of the previous aspects, wherein the temperature is from 600° C. to 1100° C.
14. The method of any of the previous aspects, wherein the contacting is carried out in the absence of catalyst.
15. The method of any of the previous aspects, wherein the contacting is carried out in the presence of catalyst.
16. The method of aspect 15, wherein the catalyst is comprised of at least one metal.
17. The method of any of aspects 15-16, wherein the catalyst is comprised of at least one transition metal.
18. The method of any of the previous aspects, wherein the first reactant is selected from the group consisting of $CHF_2Cl$, $CH_2FCl$, $CH_2ClCF_3$, $C_2H_4ClF$, $C_2H_3ClF_2$, $C_2H_2F_4$ and $C_2HCl_2F_3$.
19. The method of any of the previous aspects, wherein the second reactant is selected from the group consisting of $C_2H_3F_3$, $C_2H_4F_2$, $C_2H_5F$, $C_2H_2F_4$ and $C_2HF_5$ and chlorinated analogues thereof containing at least one Cl, at least one F and at least one H per molecule.

20. The method of any of the previous aspects, wherein the fluorinated olefin is selected from the group consisting of $F_2C=CF-CF_3$, cis $FHC=CF-CF_3$, trans $FHC=CF-CF_3$, $H_2C=CF-CF_3$, $H_2C=CCl-CF_3$, cis $ClHC=CH-CF_3$, trans $ClHC=CH-CF_3$, cis $FHC=CHCF_3$, trans $FHC=CHCF_3$ and combinations thereof.

Within this specification embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the composition or process. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method of making a fluorinated olefin comprising contacting a first reactant with a second reactant in the gas phase under an inert atmosphere at a temperature of at least 500° C., wherein:

the first reactant has structure (Ia):

  (Ia)

where X is F, Cl, Br or I and y is 1 or 2;
or structure (Ib):

  (Ib)

where X' is F, Cl, Br or I, y' is 1, 2 or 3, and z is 1 or 2; and
the second reactant has structure (II):

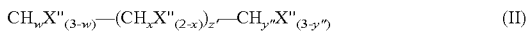  (II)

where each X" is independently selected from F, Cl, Br or I, w is 0, 1, 2 or 3, x is 0, 1 or 2, y" is 0, 1, 2 or 3, subject to the proviso that w, x and y" in structure (II) are not all 0, and z' is 0, 1 or 2.

2. The method of claim 1, wherein the second reactant contains at least one X".

3. The method of claim 1, wherein the second reactant contains at least one F.

4. The method of claim 1, wherein the first reactant has structure (Ia) and X is Cl.

5. The method of claim 1, wherein the first reactant has structure (Ib) and X' is Cl.

6. The method of claim 1, wherein z' in the second reactant is 0 or 1.

7. The method of claim 1, wherein the first reactant has structure (Ia), X is Cl and z' in the second reactant is 0 or 1.

8. The method of claim 1, wherein only one X" in the second reactant is a halide other than F.

9. The method of claim 1, wherein each X" in the second reactant is F.

10. The method of claim 1, wherein the second reactant contains at least two X" groups and each X" in the second reactant is F, subject to the proviso that one X" in the second reactant is Cl.

11. The method of claim 1, wherein the second reactant contains at least three X" groups and each X" in the second reactant is F, subject to the proviso that two X" groups are Cl.

12. The method of claim 1, wherein the temperature is from 500° C. to 1200° C.

13. The method of claim 1, wherein the temperature is from 600° C. to 1100° C.

14. The method of claim 1, wherein the contacting is carried out in the absence of catalyst.

15. The method of claim 1, wherein the contacting is can led out in the presence of catalyst.

16. The method of claim 15, wherein the catalyst is comprised of at least one metal.

17. The method of claim 15, wherein the catalyst is comprised of at least one transition metal.

18. The method of claim 1, wherein the first reactant is selected from the group consisting of CHF2Cl, CH2FCl, CH2ClCF3, C2H4ClF, C2H3ClF2, C2H2F4 and C2HCl2F3.

19. The method of claim 1, wherein the second reactant is selected from the group consisting of C2H3F3, C2H4F2, C2H5F, C2H2F4 and C2HF5 and chlorinated analogues thereof containing at least one Cl, at least one F and at least one H per molecule.

20. The method of claim 1, wherein the fluorinated olefin is selected from the group consisting of $F2C=CF-CF3$, cis $FHC=CF-CF3$, trans $FHC=CF-CF3$, $H2C=CF-CF3$, $H2C=CCl-CF3$, cis $ClHC=CH-CF3$, trans $ClHC=CH-CF3$, cis $FHC=CHCF3$, trans $FHC=CHCF3$ and combinations thereof.

* * * * *